United States Patent
Kai et al.

(10) Patent No.: US 7,605,277 B2
(45) Date of Patent: Oct. 20, 2009

(54) AMINODIBENZODIOXIN DERIVATIVE AND ORGANIC ELECTROLUMINESCENT USING THE SAME

(75) Inventors: Takahiro Kai, Fukuoka (JP); Hirokatsu Sekiya, Fukuoka (JP); Hiroshi Miyazaki, Fukuoka (JP); Shigetaka Ishikawa, Fukuoka (JP)

(73) Assignee: Nippon Steel Chemical Co., Ltd., Tokyo (JP)

( * ) Notice: Subject to any disclaimer, the term of this patent is extended or adjusted under 35 U.S.C. 154(b) by 353 days.

(21) Appl. No.: 10/588,373

(22) PCT Filed: Jan. 27, 2005

(86) PCT No.: PCT/JP2005/001079

§ 371 (c)(1), (2), (4) Date: Aug. 2, 2006

(87) PCT Pub. No.: WO2005/075451

PCT Pub. Date: Aug. 18, 2005

(65) Prior Publication Data

US 2007/0129555 A1   Jun. 7, 2007

(30) Foreign Application Priority Data

Feb. 9, 2004   (JP) ............... 2004-032380

(51) Int. Cl.
*C07D 319/00*   (2006.01)
(52) U.S. Cl. .................................... 549/359
(58) Field of Classification Search ............ 549/359
See application file for complete search history.

(56) References Cited

U.S. PATENT DOCUMENTS 5,061,569 A  10/1991  VanSlyke et al.
5,639,914 A  6/1997  Tomiyama et al.

FOREIGN PATENT DOCUMENTS

| JP | 5-078655 A | 3/1993 |
|---|---|---|
| JP | 9-157643 A | 6/1997 |
| JP | 9-194441 A | 7/1997 |
| JP | 2001-114735 A | 4/2001 |
| JP | 2001-126873 A | 5/2001 |
| JP | 2002-203685 A | 7/2002 |

OTHER PUBLICATIONS

Janietz et al, DN130:113925, 1999.*
Niume et al, DN 91:22831, 1979.*
Kelnhofer et al., *Acta Polymer*, 48, 188-192 (1997).

* cited by examiner

*Primary Examiner*—Janet L. Andres
*Assistant Examiner*—Raymond Covington
(74) *Attorney, Agent, or Firm*—Birch, Stewart, Kolasch & Birch, LLP (57) ABSTRACT

This invention relates to a highly reliable material for an organic electroluminescent element exhibiting high luminance, high luminous efficiency, little deterioration in emission, and suitability for use and storage at high temperatures and to an organic electroluminescent element using said material. The material is a diaminodibenzodioxin derivative represented by general formula (1)

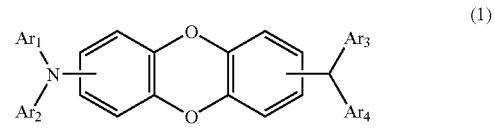

(1)

wherein $Ar_1$, $Ar_2$, $Ar_3$, and $Ar_4$ are substituted or unsubstituted aryl groups and $Ar_1$, $Ar_2$, and the nitrogen atom bonded thereto or $Ar_3$, $Ar_4$, and the nitrogen atom bonded thereto may form a nitrogen-containing heterocyclic ring; and this diaminodibenzodioxin derivative may be incorporated in the light-emitting layer, the hole-transporting layer, or the hole-injecting layer of an organic electroluminescent element.

9 Claims, 3 Drawing Sheets

AMINODIBENZODIOXIN DERIVATIVE AND ORGANIC ELECTROLUMINESCENT USING THE SAME

FIELD OF TECHNOLOGY

This invention relates to a novel aminodibenzodioxin derivative and to an organic electroluminescent element using said aminodibenzodioxin derivative.

BACKGROUND TECHNOLOGY

In the development of electroluminescent elements utilizing organic materials (hereinafter referred to as organic EL element), the kind of electrodes was optimized for the purpose of improving the charge-injecting efficiency from the electrodes and an element in which a hole-transporting layer comprising an aromatic diamine and a light-emitting layer comprising 8-hydroxyquinoline aluminum complex are disposed as thin films between the electrodes has been developed (Appl. Phys. Lett., Vol. 51, p. 913, 1987) to bring about a noticeable improvement over the conventional elements utilizing single crystals of anthracene and the like. Following this, the developmental works of organic electroluminescent elements have been focused on their commercial applications to high-performance flat panels characterized by self luminescence and high-speed response.

In order to improve the efficiency of such organic electroluminescent elements still further, various modifications of the aforementioned basic structure of anode/hole-transporting layer/light-emitting layer/cathode have been tried by suitably adding a hole-injecting layer, an electron-injecting layer, and an electron-transporting layer. For example, the following structural variations are known: anode/hole-injecting layer/hole-transporting layer/light-emitting layer/cathode; anode/hole-injecting layer/light-emitting layer/electron-transporting layer/cathode; and anode/hole-injecting layer/light-emitting layer/electron-transporting layer/electron-injecting layer/cathode. The hole-transporting layer has a function of transporting the holes injected from the hole-injecting layer to the light-emitting layer while the electron-transporting layer has a function of transporting the electrons injected from the cathode to the light-emitting layer.

The disposition of the hole-transporting layer between the light-emitting layer and the hole-injecting layer enables one to inject a larger number of holes to the light-emitting layer by applying a lower electric field. Similarly, the disposition of the electron-transporting layer between the light-emitting layer and the electron-injecting layer enables one to inject a larger number of electrons by applying a lower electric field.

A large number of organic materials conforming to the function of these layered structures have been developed. However, none of the organic EL elements using such organic materials can be said to possess satisfactory properties as yet. The largest cause therefor is insufficient durability of the materials used, particularly, the lack of durability in the materials for the hole-transporting layer. If a nonuniform portion such as a grain boundary exists in any of the organic layers of an organic El element, the electric field would converge upon that portion and eventually cause deterioration or destruction of the element. For this reason, the organic layers are often used in an amorphous condition. Moreover, an organic EL element is an element of the current injection type and it may deteriorate under the influence of the Joule heat generated during driving when the glass transition temperature (hereinafter referred to as Tg) of the materials used is low. Hence, the materials are required to have high Tg. At the same time, it is necessary to improve the luminous efficiency of the element by improving the hole-transporting capability of the hole-transporting material used therefor.

The prior technical documents relating to this invention are listed below.
Patent literature 1: JP2851185 B
Patent literature 2: JP9-194441 A
Patent literature 3: JP8-100172 A
Patent literature 4: JP2002-203685 A
Patent literature 5: JP2001-126873 A
Patent literature 6: JP2001-39333 A
Patent literature 7: JP2001-114735 A
Patent literature 8: JP9-157643 A
Non-patent literature 1: Appl. Phys. Lett., Vol. 51, p. 913, 1987
Non-patent literature 2: Appl. Phys. Lett., Vol. 57, p. 531, 1990

A variety of hole-transporting materials, triphenylamine derivatives among many, are known for organic EL elements, but few of them are suitable for practical use. For example, N,N'-bis(3-methylphenyl)-N,N'-diphenyl-4,4'-diaminobiphenyl (hereinafter referred to as TPD) is reported in Appl. Phys. Lett., Vol. 57, p. 531, 1990, but this compound lacked heat stability and caused problems in service life when used in elements.

Other examples are N,N'-dinaphthyl-N,N'-diphenyl-4,4'-diaminobiphenyl (hereinafter referred to as NPD) reported in JP2851185 B and a derivative of NPD reported in JP9-194441 A; these compounds are described to show improvements over TPD in properties, but they were not yet satisfactory in the hole-transporting capability and heat resistance. Furthermore, attempts at structural modification to improve the heat resistance are reported; for example, modification of the biphenyl skeleton in JP8-100172 A, JP2002-203685 A, JP2001-126873 A, and JP2001-29333 A and increase in quantity of arylamine units in JP2001-114735 A. However, none of such materials showed high heat resistance, good stability of thin film, and high luminous efficiency at the same time.

As described above, the conventional organic EL materials for the hole-transporting and other functions of organic EL elements do not possess satisfactory properties suitable for practical use and there are expectations that the use of materials of better properties would improve the efficiency, heat resistance, and service life of organic EL elements. Now, in the majority of organic El elements, light is emitted mostly from the light-emitting layer that is provided separately from the charge-transporting layer or from the electron-transporting layer and rarely from the hole-transporting layer. This may be due partly to the problem of compatibility of the hole-transporting layer with the simultaneously used electron-transporting layer, but a factor just as important appears to be the color and intensity of the light emitted from the hole-transporting material itself. The hole-transporting layer is expected to increase in practical value if light can be emitted therefrom, but materials useful for this purpose are few. As represented by the 9-anthranyl derivatives described in JP9-157643 A, the materials of this kind in many cases have faced problems such as emission of light of long wavelength and no emission of light of short wavelength.

DISCLOSURE OF THE INVENTION

Problems to be Solved by the Invention

This invention has been worked out to solve the aforementioned problems concerning the conventional technology and its object is to provide an organic electroluminescent element with high luminous efficiency, high heat resistance and long service life and further provide novel compounds and organic electroluminescent materials for said elements.

Means to Solve the Problems

The inventors of this invention have conducted intensive studies to solve the aforementioned problems concerning the conventional technology, found specific aminodibenzodioxin derivatives and their successful use in obtaining organic EL elements with high efficiency, high heat resistance and long service life, and completed this invention.

Accordingly, this invention relates to an aminodibenzodioxin derivative represented by general formula (1).

In general formula (1), $Ar_1$, $Ar_2$, $Ar_3$, and $Ar_4$ are independently substituted or unsubstituted aryl groups and $Ar_1$, $Ar_2$ and the nitrogen atom bonded thereto or $Ar_3$, $Ar_4$ and the nitrogen atom bonded thereto may form a nitrogen-containing heterocyclic ring.

Furthermore, this invention relates to an organic electroluminescent element comprising an anode, organic layers, and a cathode placed one upon another on a substrate and at least one of the organic layers comprises the aforementioned aminodibenzodioxin derivative. The organic layer comprising the aminodibenzodioxin derivative is preferably at least one layer selected from the group of the light-emitting layer, hole-transporting layer, and hole-injecting layer.

Firstly, the aminodibenzodioxin derivatives to be used in this invention will be explained.

The aminodibenzodioxin derivatives are represented by general formula (1). In the formula, $Ar_1$, $Ar_2$, $Ar_3$, and $Ar_4$ are substituted or unsubstituted aryl groups. The unsubstituted aryl groups here mean carbocyclic aromatic groups such as phenyl, naphthyl, anthryl, and phenanthryl and heterocyclic aromatic groups such as furyl, thienyl, and pyridyl. Preferably, they are carbocyclic aromatic groups containing 6 to 18 carbon atoms or heterocyclic aromatic groups containing 4 to 17 carbon atoms and 1 to 4 hetero atoms. The aryl groups have 1 to 4 rings, preferably 1 to 3 rings, and they may be condensed or uncondensed.

More preferably, $Ar_1$, $Ar_2$, $Ar_3$, and $Ar_4$ are independently carbocyclic aromatic groups of 6 to 16 carbon atoms or heterocyclic aromatic groups of 4 to 14 carbon atoms, either unsubstituted or substituted with alkyl groups, alkoxy groups, aryl groups of 4 to 12 carbon atoms, or aryloxy groups of 4 to 12 carbon atoms. In the case of heterocyclic aromatic groups, the hetero atoms involved are N, S, O, and the like and the sum of the number of hetero atoms is preferably in the range of 1 to 4. It is just as desirable that $Ar_1$, $Ar_2$, $Ar_3$, and $Ar_4$ are independently phenyl, naphthyl, or phenanthryl group, either unsubstituted or substituted with lower alkyl groups, lower alkoxy groups, aryl groups of 4 to 10 carbon atoms, or aryloxy groups of 4 to 10 carbon atoms.

Moreover, $Ar_1$, $Ar_2$, and the nitrogen atom bonded thereto or $Ar_3$, $Ar_4$, and the nitrogen atom bonded thereto may form a nitrogen-containing heterocyclic ring. In this case, the rings formed from —$NAr_1Ar_2$ and —$NAr_3Ar_4$ represent groups such as substituted or unsubstituted N-carbazolyl, N-phenoxadinyl, N-phenothiazinyl, and N-β-carbolinyl.

Concretely, the unsubstituted $Ar_1$, $Ar_2$, $Ar_3$, and $Ar_4$ groups include phenyl, naphthyl, phenanthryl, indenyl, azulenyl, heptalenyl, acenaphthylenyl, phenalenyl, fluorenyl, anthryl, biphenylenyl, triphenylenyl, tetraphenylenyl, pyrenyl, chrysenyl, picenyl, perylenyl, pentaphenyl, pentacenyl, hexaphenyl, hexacenyl, rubicenyl, coronenyl, trinaphthylenyl, heptaphenyl, heptacenyl, pyranthrenyl, ovalenyl, furyl, thienyl, pyridyl, carbazolyl, thianthrenyl, pyranyl, isobenzofuranyl, chromenyl, xanthenyl, phenoxathinyl, pyrrolyl, imidazolyl, pyrazolyl, isothiazolyl, isoxazolyl, pyrazinyl, pyrimidinyl, pyridazinyl, indolidinyl, isoindolyl, purinyl, indolyl, quinolyl, isoquinolyl, acridinyl, phenathrolinyl, phthalazinyl, naphthyridinyl, quinoxalinyl, quinazolinyl, phenanthridinyl, perimidinyl, phenanthrolinyl, phenazinyl, and furazanyl. Of the groups listed above, phenyl, naphthyl, phenanthryl, indenyl, fluorenyl, anthryl, pyrenyl, perylenyl, pentaphenyl, coronenyl, furyl, thienyl, pyridyl, carbazolyl, pyranyl, pyrrolyl, imidazolyl, pyrazolyl, isothiazolyl, isoxazolyl, pyrimidinyl, indolidinyl, indolyl, quinolyl, isoquinolyl, acridinyl, phenanthrolinyl, quinoxalinyl, quinazolinyl, and phenazinyl are preferred and phenyl, naphthyl, and phenanthryl are more preferred.

The substituents in the substituted $Ar_1$, $Ar_2$, $Ar_3$, and $Ar_4$ groups include nitro, cyano, alkyl, aralkyl, aralkyloxy, alkoxy, aryl, and aryloxy groups. Concretely, the alkyl groups include methyl, ethyl, propyl, isopropyl, butyl, sec-butyl, tert-butyl, pentyl, hexyl, heptyl, octyl, and stearyl; the aralkyl groups include 2-phenylisopropyl, benzyl, and triphenylmethyl; the alkoxy groups include methoxy, ethoxy, propoxy, n-butoxy, sec-butoxy, tert-butoxy, pentyloxy, hexyloxy, n-octyloxy, tert-octyloxy, and stearyloxy; the aralkyloxy groups include benzyloxy; the aryl groups include phenyl, biphenylyl, naphthyl, phenanthryl, indenyl, azulenyl, heptalenyl, acenaphthylenyl, phenalenyl, fluorenyl, anthryl, biphenylenyl, triphenylenyl, tetraphenylenyl, pyrenyl, chrysenyl, picenyl, perylenyl, pentaphenyl, pentacenyl, hexaphenyl, hexacenyl, rubicenyl, coronenyl, trinaphthylenyl, heptaphenyl, heptacenyl, pyranthrenyl, ovalenyl, furyl, thienyl, pyridyl, carbazolyl, thianthrenyl, pyranyl, isobenzofuranyl, chromenyl, xanthenyl, phenoxathinyl, pyrrolyl, imidazolyl, pyrazolyl, isothiazolyl, isoxazolyl, pyrazinyl, pyrimidinyl, pyridazinyl, indolidinyl, isoindolyl, purinyl, indolyl, quinolyl, isoquinolyl, acridinyl, phenanthrolinyl, phthalazinyl, naphthyridinyl, quinoxalinyl, quinazolinyl, phenanthridinyl, perimidinyl, phenanthrolinyl, phenazinyl, furazanyl, 4-methylbiphenylyl, 3-nitrophenyl, 4-cyanophenyl, o-methoxyphenyl, m-methoxyphenyl, p-methoxyphenyl, o-tolyl, m-tolyl, p-tolyl, o-cumenyl, m-cumenyl, p-cumenyl, mesityl, 4-phenoxyphenyl, and 5-methylnaphthyl; the aryloxy groups include those aryloxy groups which are derived from the aforementioned aryl groups. These substituents may be newly bonded to the neighboring substituents to form saturated or aromatic rings.

The aminodibenzodioxin derivatives to be used in this invention have a structure formed by substituting the dibenzodioxin ring with —$NAr_1Ar_2$ and —$NAr_3Ar_4$ and this substitution may occur at the positions 1 and 5, 1 and 6, 1 and 7, 1 and 8, 2 and 6, or 2 and 7, preferably at 2 and 6, 1 and 5, or 2 and 7, more preferably at 2 and 6.

Typical examples of such aminodibenzodioxin derivatives are listed in Tables 1 to 4, but this invention is not limited to these examples.

TABLE 1

TABLE 1-continued

| Compd. No. | Ar₁ | Ar₂ | Ar₃ | Ar₄ |
|---|---|---|---|---|
| 9 | 1-naphthyl | 2-naphthyl | 1-naphthyl | 2-naphthyl |
| 10 | 1-naphthyl | 1-naphthyl | 1-naphthyl | 1-naphthyl |
| 11 | 1-naphthyl | 4-isoquinolyl | 1-naphthyl | 4-isoquinolyl |
| 12 | 1-naphthyl | 5-(1,10-phenanthrolyl) | 1-naphthyl | 5-(1,10-phenanthrolyl) |

TABLE 2

| Compd. No. | Ar1 | Ar2 | Ar3 | Ar4 |
|---|---|---|---|---|
| 13 | 9-phenanthryl | 2,4-dimethylphenyl | 9-phenanthryl | 2,4-dimethylphenyl |
| 14 | 9-phenanthryl | 3,4-dimethoxyphenyl | 9-phenanthryl | 3,4-dimethoxyphenyl |

TABLE 2-continued

| Compd. No. | Ar1 | Ar2 | Ar3 | Ar4 |
|---|---|---|---|---|
| 15 |  |  |  |  |
| 16 |  |  |  |  |
| 17 |  |  |  |  |
| 18 |  |  |  |  |
| 19 |  |  |  |  |
| 20 |  |  |  |  |
| 21 |  |  |  |  |
| 22 |  |  |  | |

TABLE 2-continued

| Compd. No. | Ar1 | Ar2 | Ar3 | Ar4 |
|---|---|---|---|---|
| 23 | |  | |  |
| 24 | |  |  |  |
| 25 | |  |  |  |

TABLE 3

| Compd. NO. | Ar₁ | Ar₂ | Ar₃ | Ar₄ |
|---|---|---|---|---|
| 26 |  |  |  |  |
| 27 |  |  |  |  |
| 28 |  |  | | |

TABLE 3-continued

| Compd. NO. | Ar₁ | Ar₂ | Ar₃ | Ar₄ |
|---|---|---|---|---|
| 29 | phenanthrenyl | pyridinyl | phenanthrenyl | pyridinyl |
| 30 | fluorenyl | | fluorenyl | |

TABLE 4

| Compd. No. | Ar₁ | Ar₂ | Ar₃ | Ar₄ |
|---|---|---|---|---|
| 31 | phenyl | naphthyl | phenyl | naphthyl |
| 32 | phenyl | phenanthrenyl | phenyl | phenanthrenyl |
| 33 | naphthyl | dimethoxyphenyl (OMe, OMe) | naphthyl | dimethoxyphenyl (OMe, OMe) |
| 34 | phenanthrenyl | pyridinyl | phenanthrenyl | pyridinyl |
| 35 | fluorenyl | | fluorenyl | |

The presence of a dibenzodioxin ring in the compounds to be used in this invention accounts for increased rigidity compared with the compounds having a biphenylene skeleton represented by NPD. Increased rigidity expresses itself as an increase in glass transition temperature thereby producing an improvement in resistance to the Joule heat generated in the organic layers, between the organic layers, or between the organic layer and the metal electrode during electroluminescence and in heat resistance in a high-temperature environment. Therefore, these compounds are used advantageously in organic EL elements as a hole-transporting layer, a light-emitting material, a host material in the light-emitting layer, a dopant in the light-emitting layer, a hole-blocking layer, or an electron-transporting layer to emit light over a prolonged period of time.

Furthermore, these compounds having a dibenzodioxin ring as the basic skeleton can be formed into amorphous films that are homogeneous and stable. This helps to solve the problems hitherto associated with the conventional non-homogeneous amorphous films, that is, the decrease in luminous efficiency and deterioration of the element.

Still further, the compounds show higher luminous efficiency than the conventionally used compounds in addition to the aforementioned heat stability and thin film stability.

It is generally desirable that a compound to be used in one of the organic layers constituting an organic EL element does not form an excited complex with a compound used in another of the organic layers and the aminodibenzodioxin derivatives used in this invention have the advantage of difficultly forming excited complexes with other compounds.

One of the methods for synthesizing a compound represented by general formula (1) in this invention consists of carrying out the reaction of a diaminodibenzodioxin with an aryl halide in an organic solvent or solventless in the presence of a base and a catalyst in an atmosphere of nitrogen at a temperature in the range of 100 to 200° C. for a period of 1 to 50 hours. The halogen atom in the aryl halide may be chlorine, bromine, or iodine. The bases useful for the reaction include inorganic bases such as potassium carbonate, sodium carbonate, lithium hydroxide, sodium hydroxide, sodium tert-butoxide, and potassium tert-butoxide and organic bases such as pyridine, picoline and triethylamine. The catalysts include copper-based catalysts such as copper powder, copper oxide, copper halides, and copper sulfate and palladium complex-based catalysts comprising a palladium source such as palladium acetate and bis(dibenzylideneacetone)palladium and a ligand such as tri-tert-butylphosphine. The solvent may be any compound which is capable of dissolving the raw materials and letting the reaction to proceed; for example, toluene, xylene, tetralin, quinoline, nitrobenzene, dimethyl sulfoxide, and N,N-dimethylformamide.

Upon completion of the reaction, the organic layer is separated by addition of water, concentrated, washed with a low-boiling solvent such as ethyl acetate, and dried under reduced pressure to give a compound useful for this invention. In case the compound is used as an organic El material, it is preferably purified further by sublimation.

The organic EL element to be prepared according to this invention is next explained.

An organic EL element in this invention may assume a variety of structures, but basically it comprises an organic layer containing the aforementioned aminodibenzodioxin derivative disposed between a pair of electrodes (cathode and anode). An aminodibenzodioxin derivative alone can be used as a hole-injecting layer, hole-transporting layer, light-emitting layer, hole-blocking layer, electron-injecting layer, or electron-transporting layer and, if desirable, another hole-injecting material, hole-transporting material, hole-blocking material, light-emitting material, electron-injecting material, or electron-transporting material can be added to layer comprising the aforementioned aminodibenzodioxin derivative. In particular, when an aminodibenzodioxin derivative is used as a light-emitting layer, addition of another light-emitting material makes it possible to emit light of different wavelength or improve the luminous efficiency. It is further possible to form a hole-injecting material, hole-transporting material, light-emitting material, hole-blocking material, electron-injecting material, or electron-transporting material respectively into a hole-injecting layer, hole-transporting layer, light-emitting layer, hole-blocking layer, electron-injecting layer, or electron-transporting layer and laminate the layer thus formed to the layer comprising an aminodibenzodioxin derivative.

Examples of the layered structures are listed below:
1) anode/organic light-emitting layer/cathode,
2) anode/hole-transporting layer/organic light-emitting layer/cathode,
3) anode/hole-transporting layer/organic light-emitting layer/hole-blocking layer/cathode,
4) anode/hole-injecting layer/hole-transporting layer/organic light-emitting layer/cathode,
5) anode/hole-injecting layer/hole-transporting layer/organic light-emitting layer/hole-blocking layer/cathode,
6) anode/organic light-emitting layer/electron-transporting layer/cathode,
7) anode/organic light-emitting layer/electron-transporting layer/electron-injecting layer/cathode,
8) anode/organic light-emitting layer/hole-blocking layer/electron-transporting layer/electron-injecting layer/cathode,
9) anode/hole-transporting layer/organic light-emitting layer/hole-blocking layer/electron-transporting layer/cathode,
10) anode/hole-injecting layer/hole-transporting layer/organic light-emitting layer/electron-transporting layer/cathode,
11) anode/hole-injecting layer/hole-transporting layer/organic light-emitting layer/electron-transporting layer/hole-blocking layer/cathode,
12) anode/hole-injecting layer/hole-transporting layer/organic light-emitting layer/electron-transporting layer/electron-injecting layer/cathode, and
13) anode/hole-injecting layer/hole-transporting layer/organic light-emitting layer/hole-blocking layer/electron-transporting layer/electron-injecting layer/cathode.

The hole-injecting layer, the electron-injecting layer and the hole-blocking layer in these layered structures are not always necessary, but providing these layers helps to improve the luminous efficiency.

An organic EL element in this invention may assume any of the aforementioned structures, but it is preferably supported on a substrate.

A plate of quartz or glass, a metallic plate or foil, or a plastic film or sheet is used as a substrate. In particular, a plate of glass or a plate of transparent synthetic resin such as polyester, polymethacrylate, polycarbonate, and polysulfone is preferred. When a synthetic resin substrate is used, it is necessary to take the gas barrier property into consideration. When the gas barrier property of the chosen substrate is poor, the air passing through the substrate may undesirably deteriorate the organic electroluminescent element. One of the desirable methods for securing the gas barrier property is to provide a dense silicon oxide film on at least one side of the synthetic resin substrate.

The anode is composed of a metal such as aluminum, gold, silver, nickel, palladium, and platinum, a metal oxide such as oxide of indium and/or tin, a metal halide such as copper iodide, carbon black, or an electrically conductive polymer such as poly(3-methylthiophene), polypyrrole, and polyaniline. The anode is formed mostly by sputtering or vacuum deposition. In the case where the material chosen for the anode is a metal such as silver, copper iodide, carbon black, a conductive metal oxide, or a conductive polymer, respectively in fine particles, the particles are dispersed in a solution of a suitable binder resin and applied to a substrate to form the anode. Moreover, in the case of a conductive polymer, the anode is formed by electrolytically polymerizing the corresponding monomer in thin film directly on a substrate or by coating a substrate with the polymer. It is also possible to form the anode by laminating different materials. The thickness of the anode varies with the requirement for transparency. Where transparency is required, it is desirable to control the transmission of visible light normally at 60% or more, preferably at 80% or more; in this case, the thickness is normally 5 to 1000 nm, preferably 10 to 500 nm. Where opaqueness is tolerated, the anode may be the same as the substrate. Furthermore, it is possible to laminate a different conductive material to the aforementioned anode.

The material for the cathode may be the same as the one used for the aforementioned anode. However, it is desirable to use a metal of low work function in order to inject electrons efficiently. Such metals include tin, magnesium, indium, calcium, aluminum, and silver and their alloys. Concrete examples are electrodes made from alloys of low work function such as magnesium-silver alloy, magnesium-indium alloy, and aluminum-lithium alloy. Insertion of an ultrathin insulating film (0.1 to 5 nm) of LiF, $MgF_2$, $LiO_2$, and the like in the interface between the cathode and the electron-transporting layer is an effective method for improving the efficiency of the element. The thickness of the cathode is normally the same as that of the anode. Lamination of a metal of high work function and good stability against the air to the cathode made from a metal of low work function for the purpose of protecting the cathode increases the stability of the element. A metal such as aluminum, silver, copper, nickel, chromium, gold, and platinum is used for this purpose.

The organic materials to be used as hole-injecting materials, hole-transporting materials, light-emitting materials, hole-blocking materials, electron-injecting materials, and electron-transporting materials in the organic EL elements according to this invention preferably show a Tg of 80° C. or above, more preferably 100° C. or above.

The hole-injecting material must satisfy the requirements of good contact with the anode, formability into a uniform film, and thermal stability, that is, the material is required to have a melting point of 300° C. or above and a glass transition temperature of 100° C. or above. Additional requirements are low ionization potential to facilitate the injection of holes from the anode and high hole mobility.

The following compounds have been reported to satisfy the aforementioned requirements and can be used as hole-injecting materials; phthalocyanine compounds such as copper phthalocyanine, organic compounds such as polyaniline and polythiophene, sputtered carbon membranes, and metal oxides such as vanadium oxide, ruthenium oxide, and molybdenum oxide. In the case of an anode buffer layer, a thin film can be made as in the hole-transporting layer and, where the layer is made from an inorganic material, a technique such as sputtering, electron beam deposition, and plasma CVD can be used. The thickness of the hole-injecting layer formed in the aforementioned manner is normally 3 to 100 nm, preferably 5 to 50 nm.

The hole-transporting material is required to show high efficiency in the injection of holes from the hole-injecting layer and in the transportation of the injected holes. This means that the material is required to satisfy the following requirements; it has a low ionization potential, it readily transmits visible light, it shows a high hole mobility, it is stable, and it generates with difficulty during manufacture or use the impurities which become traps. As the material contacts the light-emitting layer, it is further required not to quench the light from the light-emitting layer nor to lower the efficiency by forming an exciplex with the light-emitting layer. In addition to the aforementioned general requirements, the elements in vehicular applications are required to be heat-resistant and the material should desirably show a Tg of 90° C. or above.

The compounds known as the hole-transporting materials of this kind include aromatic diamines containing two or more tertiary amines whose nitrogen atoms bear two or more condensed aromatic rings, a typical example being 4,4'-bis[N-(1-naphthyl)-N-phenylamino]biphenyl, aromatic amines of a starburst structure such as 4,4',4"-tris(1-naphthylphenylamino)triphenylamine, an aromatic amine consisting of a tetramer of triphenylamine, and spiro compounds such as 2,2',7,7'-tetrakis-(diphenylamino)-9,9'-spirobifluorene. They can be used singly or, if necessary, as a mixture.

Besides the aforementioned compounds, polymers such as polyvinylcarbazole, polyvinyltriphenylamine, and polyaryleneethersulfones containing tetraphenylbenzidine are used as materials for the hole-transporting layer.

Where the coating process is used to provide the hole-transporting layer, one kind or two kinds or more of hole-transporting materials is dissolved, if necessary, together with additives such as binder resins that do not form traps of holes and improvers of coating properties, and the coating solution is applied by the spin coating process to the surface of the hole-injecting layer and dried. The binder resins of this kind include polycarbonate, polyarylate, and polyester. The binder resin, when added in excess, decreases the hole mobility and it is desirably added in a smaller amount, normally, below 50 wt %.

Where the vacuum deposition process is used, a hole-transporting material is introduced to a crucible provided inside a vacuum vessel, the vessel is evacuated to $10^{-4}$ Pa or so by a suitable vacuum pump, the crucible is heated to vaporize the hole-transporting material, and the vapor is deposited on a substrate which is equipped with an anode and placed opposite the crucible to form the hole-transporting layer. The thickness of the hole-transporting layer is normally 5 to 300 nm, preferably 10 to 100 nm. A film as thin as this is usually formed by the vacuum deposition technique.

Light-emitting materials are made up of singlet light-emitting materials and triplet light-emitting materials. Besides Alq3 and its derivatives, publicly known light-emitting materials such as daylight fluorescent materials, fluorescent brighteners, laser pigments, organic scintillators, and a variety of reagents for fluorimetry can be used as singlet light-emitting materials.

Concretely, the singlet light-emitting materials include polycyclic condensed compounds such as anthracene, pyrene, chrysene, perylene, coronene, rubrene, and quinacridone, oligophenylene compounds such as quarterphenyl, scintillators for use in liquid scintillation such as 1,4-bis(2-methylstyryl)benzene, 1,4-bis(4-methyl-5-phenyl-2-oxazolyl)benzene, 1,4-bis(5-phenyl-2-oxazolyl)benzene, 2,5- bis(5-tert-butyl-2-benzoxazolyl)thiophene, 1,4-diphenyl-1,3-butadiene, 1,6-diphenyl-1,3,5-hexatriene, and 1,1,4,4-tetraphenyl-1,3-butadiene, metal complexes of oxine derivatives, coumarin dyes, dicyanomethylenepyran dyes, dicyanomethylenethiopyran dyes, polymethine dyes, oxobenzanthracene dyes, xanthene dyes, carbostyryl dyes, perylene dyes, oxadine-based compounds, stilbene derivatives, spiro compounds, and oxadiazole-based compounds.

On the other hand, the triplet light-emitting materials include noble metal complexes comprising platinum or iridium as central metal. The content of the metal complex of this kind in the light-emitting layer is preferably in the range of 0.1 to 30 wt%. A content of less than 0.1 wt% cannot contribute to improve the luminous efficiency of the element while a content in excess of 30 wt% causes concentration quenching due to dimerization of the organic metal complexes themselves and eventual decrease in the luminous efficiency. In the conventional elements utilizing fluorescence (singlet), the use of the organic metal complex in an amount somewhat greater than the fluorescent pigment (dopant) contained in the light-emitting layer seems desirable. The organic metal complex in the light-emitting layer may be contained partly or distributed non-uniformly in the direction of the film thickness. The thickness of the light-emitting layer is normally 10 to 200 nm, preferably 20 to 100 nm.

The hole-blocking material is placed in contact with the interface on the cathode side of the light-emitting layer and comprises a compound capable of blocking the holes migrating from the hole-transporting layer to reach the cathode and transporting the electrons injected from the cathode efficiently to the light-emitting layer. The properties required for the materials constituting the hole-blocking layer are high electron mobility and low hole mobility. The hole-blocking layer has a function of confining holes and electrons in the light-emitting layer and improving the luminous efficiency.

The electron-transporting layer is composed of a compound that is capable of transporting the electrons injected from the cathode efficiently toward the hole-blocking layer when an electric field is applied to the electrodes. The electron-transporting materials for use in the electron-transporting layer of an organic EL element according to this invention are compounds that are required to inject electrons efficiently from the cathode, show high electron mobility, and have the ability to transport efficiently the injected electrons.

The materials satisfying these requirements include metal complexes such as 8-hydroxyquinoline aluminum complex, metal complexes of 10-hydroxybenzo[h]quinoline, oxadiazole derivatives, distyrylbiphenyl derivatives, silole derivatives, 3- or 5-hydroxyflavone metal complexes, benzoxazole metal complexes, benzothiazole metal complexes, trisbenzimidazolylbenzene, quinoxaline compounds, phenanthroline derivatives, 2-tert-butyl-9,10-N,N'-dicyanoanthraquinonediimine, n-type hydrogenated amorphous silicon carbide, n-type zinc sulfide, and n-type zinc selenide. The thickness of the electron-transporting layer is normally 5 to 200 nm, preferably 10 to 100 nm.

The electron-transporting layer is formed on the hole-blocking layer by coating or vacuum deposition, usually the latter, as in the formation of the hole-transporting layer.

According to this invention, an organic EL element comprises compounds specified by this invention in its organic layers, preferably in its light-emitting layer, hole-transporting layer, or hole-injecting layer.

EXPLANATION OF THE SYMBOLS

1: Glass substrate, 2: Anode (ITO layer), 3: CuPc layer, 4: Hole-transporting layer, 5: Light-emitting and electron-transporting layer, 6: Cathode (LiF/Al)

PREFERRED EMBODIMENTS OF THE INVENTION

This invention will be described in detail below with reference to the accompanying Synthetic Examples and Examples, but it will not be limited to these examples unless it exceeds its substance.

Compounds Nos. 2 and 3 were prepared in accordance with the following synthetic route. The compound number corresponds to that in Tables 1 to 4.

Synthetic Example 1

Synthesis of 2,6-dinitrodibenzodioxin

To 1600 ml of acetic acid was added 60 g (0.326 mole) of dibenzodioxin, and 280 ml of fuming nitric acid was added in drops to the mixture over a period of 1 hour with stirring at room temperature. Upon completion of the dropwise addition, the mixture was stirred for another 2 hours and a precipitate was recovered by filtration. The precipitate was turned into a slurry by methanol and dried under reduced pressure to give 85.7 g (0.313 mole) of 2,6-dinitrodibenzodioxin in a 96.0% yield. The product showed a purity of 96.5 area % (HPLC, 254 nm).

Synthetic Example 2

Synthesis of 2,6-diaminodibenzodioxin

To a mixture of 1000 ml of anisole and 1000 ml of THF were added 81 g (0.295 mole) of 2,6-dinitrodibenzodioxin and 25 g of 10% palladium/carbon and hydrogen gas was passed through the mixture for 8 hours at room temperature with stirring. The 10% palladium/carbon was filtered and rinsed with THF. The filtrate and the rinsings were mixed, concentrated, and dried under reduced pressure to give 61.9 g (0.289 mole) of 2,6-diaminodibenzodioxin in a 98.0% yield. The product showed a purity of 94.2 area % (HPLC, 254 nm).

Synthetic Example 3

Synthesis of N,N'-diacetyl-2,6-diaminodibenzodioxin

To a mixture of 900 ml of toluene and 900 ml of THF were added 50.0 g (0.233 mole) of 2,6-diaminodibenzodioxin and 55.3 g (0.699 mole) of pyridine and 59.5 g (0.583 mole) of anhydrous acetic acid was added in drops to the mixture over a period of 10 minutes with stirring at room temperature. After the dropwise addition was over, the mixture was stirred overnight and a precipitate was recovered by filtration. The precipitate was submitted to reslurrying with toluene (250 ml×2) and then dried under reduced pressure to give 57.0 g (0.191 mole) of N,N'-diacetyl-2,6-diaminodibenzodioxin in an 82.0% yield. The product showed a purity of 99.3 area % (HPLC, 254 nm).

Synthetic Example 4

Synthesis of N,N'-diacetyl-N,N'-diphenyl-2,6-diaminodibenzodioxin

A slurry prepared from 34.3 g (0.115 mole) of N,N'-diacetyl-2,6-diaminodibenzodioxin, 96.4 g (0.576 mole) of iodobenzene, 48.2 g (0.253 mole) of copper (I) iodide, 63.6 g (0.460 mole) of potassium carbonate, and 1500 ml of quinoline was heated with stirring at 170° C. for 48 hours. The slurry was cooled to room temperature, 500 ml of methylene chloride and 500 ml of water were added, and a precipitate was filtered off. To the filtrate was added 500 ml of water and the organic layer was separated from the aqueous layer. The organic layer was concentrated and dried under reduced pressure to give 79.4 g of a crude product. The product was used without purification in the next reaction.

Synthetic Example 5

Synthesis of N,N'-diphenyl-2,6-diaminodibenzodioxin

To a mixture of 500 g of methanol and 100 g of a 25% aqueous solution of sodium hydroxide was added 79.4 g of the diacetoamide compound obtained in Synthetic Example 4 and the mixture was heated under reflux for 20 hours. The reaction mixture was cooled to room temperature, 1000 ml of water was added, and a precipitate was recovered by filtration. The precipitate was rinsed with water and dried under reduced pressure to give 44.3 g of N,N'-diphenyl-2,6-diaminodibenzodioxin. The crude product thus obtained was purified by reslurrying under heat with methanol (2 steps) to give 31.8 g (0.087 mole) of the product with a purity of 98.4 area % (HPLC, 254 nm) in a 75.7% yield.

EXAMPLES

Example 1

Synthesis of N,N'-di(1-naphthyl)-N,N'-diphenyl-2,6-diaminodibenzodioxin (compound No. 2)

To a solution of 0.161 g (0.715 mmole) of palladium (II) acetate in 20 ml of xylene was added 0.58 g (2.86 mmoles) of tri-tert-butylphosphine and heated at 80° C. for 30 minutes. The resulting solution was forwarded into a solution heated at 80° C. of 5.24 g (0.0143 mole) of N,N'-diphenyl-2,6-diaminodibenzodioxin, 7.41 g (0.0358 mole) of 1-bromonaphthalene, and 5.77 g (0.06 mole) of sodium tert-butoxide in 260 ml of xylene. The mixture was then heated up to 135° C. and further heated at this temperature with stirring for 4 hours. The mixture was cooled to room temperature, 200 ml of water was added, and the aqueous layer was separated from the organic layer. The aqueous layer was washed with 200 ml of toluene, the toluene washing was mixed with the organic layer, the mixture was concentrated and dried under reduced pressure to give 9.5 g of a crude product. The crude product was subjected to reslurrying under heat with ethyl acetate and dried under reduced pressure to give 3.40 g (0.0055 mole) of N,N'-di(1-naphthyl)-N,N'-diphenyl-2,6-diaminodibenzodioxin in a 38.5% yield. The product thus obtained showed a purity of 98.3 area % (HPLC, 254 nm). The product was further purified by sublimation.

The structure of this product was confirmed by $^1$H-NMR (solvent, THF-d8), $^{13}$C-NMR (solvent, THF-d8), and IR.

Figure 1:
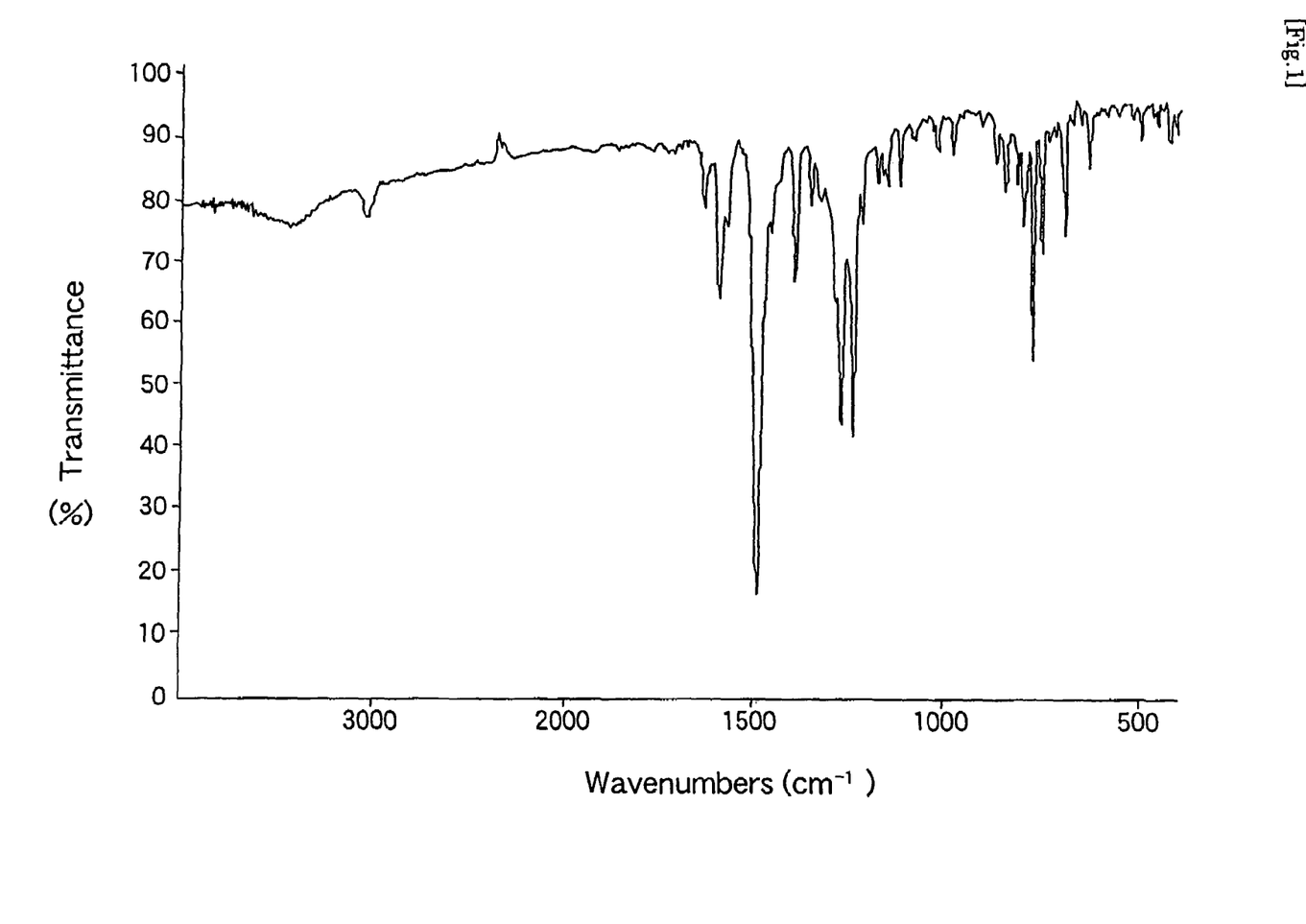
FIG. 1 shows the IR spectrum of compound No. 2.

The IR spectrum of compound No. 2 is shown in FIG. 1.

Example 2

Synthesis of N,N'-di(9-phenanthryl)-N,N'-diphenyl-2,6-diaminodibenzodioxin (compound No. 3)

To a solution of 0.12 g (0.55 mole) of palladium (II) acetate in 10 ml of xylene was added 0.445 g (2.2 mmoles) of tri-tert-butylphosphine and the mixture was heated at 80° C. with stirring for 30 minutes. This solution was forwarded into a solution heated at 80° C. of 4.03 g (0.011 mole) of N,N'-diphenyl-2,6-diaminodibenzodioxin, 7.07 g (0.0275 mole) of 9-bromophenanthrene, and 4.44 g (0.0462 mole) of sodium tert-butoxide in 200 ml of xylene. The solution was then heated up to 135° C. and further heated at this temperature with stirring for 3 hours. The mixture was cooled to room temperature, 150 ml of water was added, and a precipitate was filtered off. The mother liquor was separated into the aqueous and organic layers, the aqueous layer was washed with 200 ml of toluene, the toluene washing was mixed with the organic layer, and the mixture was concentrated and dried under reduced pressure to give 13.0 g of a crude product. The crude product was treated with activated carbon and crystallized from ethyl acetate/hexane to give 3.85 g (0.00536 mole) of N,N'-di(9-phenanthryl)-N,N'-diphenyl-2,6-diaminodibenzodioxin in a 48.7% yield. The product showed a purity of 98.6 area % (HPLC, 254 nm). The product was further purified by sublimation.

The structure of this product was confirmed by $^1$H-NMR (solvent, THF-d8), $^{13}$C-NMR (solvent, THF-d8), and IR.

Figure 2:
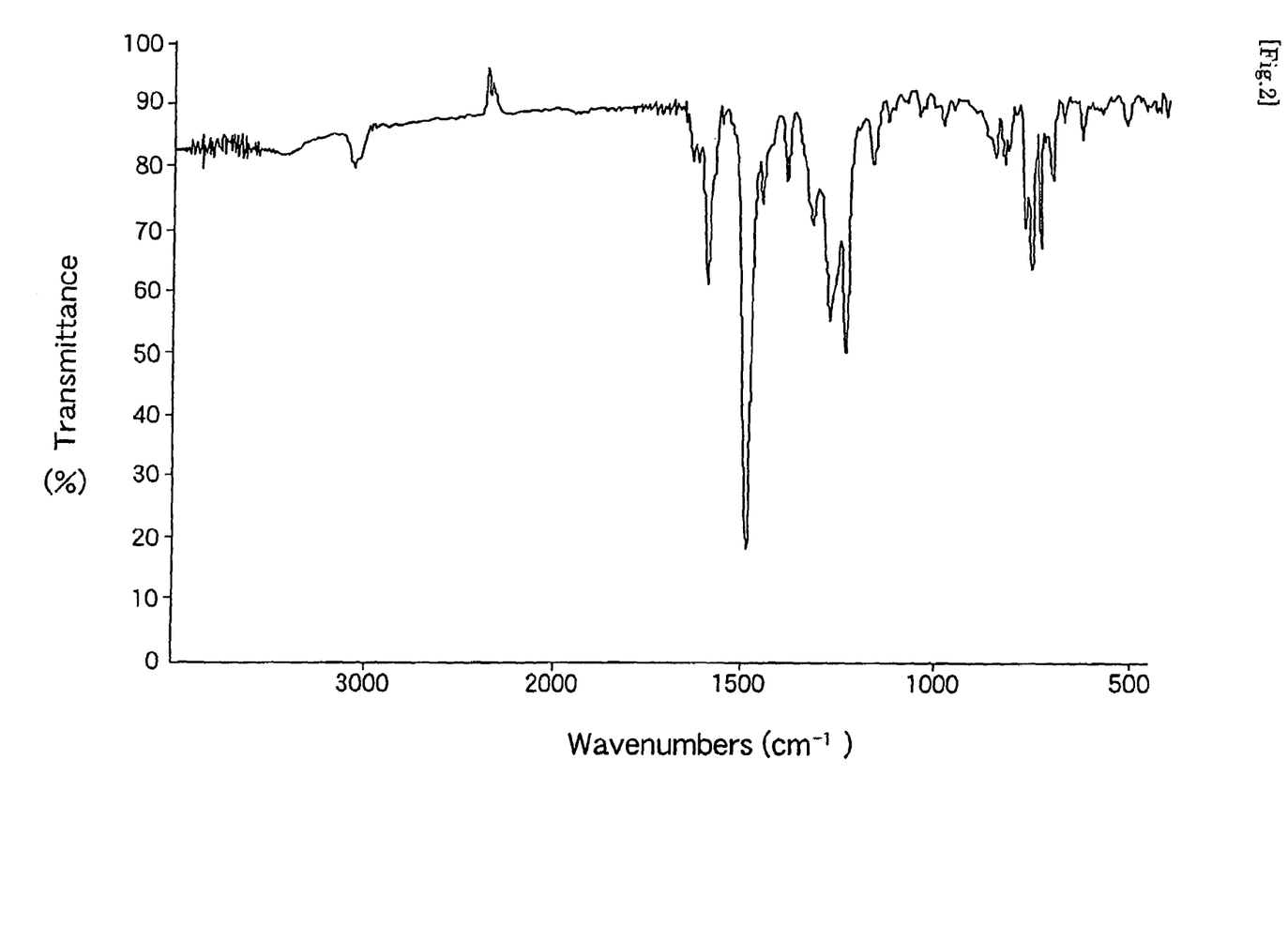
FIG. 2 shows the IR spectrum of compound No. 3.

The IR spectrum of compound No. 3 is shown in FIG. 2.

The glass transition temperature was measured for the compounds No. 2 and No. 3 obtained in the aforementioned examples and for the known hole-transporting material NPD and the results are shown in Table 5.

TABLE 5

| hole-transporting material | glass transition temperature (° C.) |
|---|---|
| Compound 2 | 103 |
| Compound 3 | 149 |
| NPD | 98 |

Example 3

Figure 3:
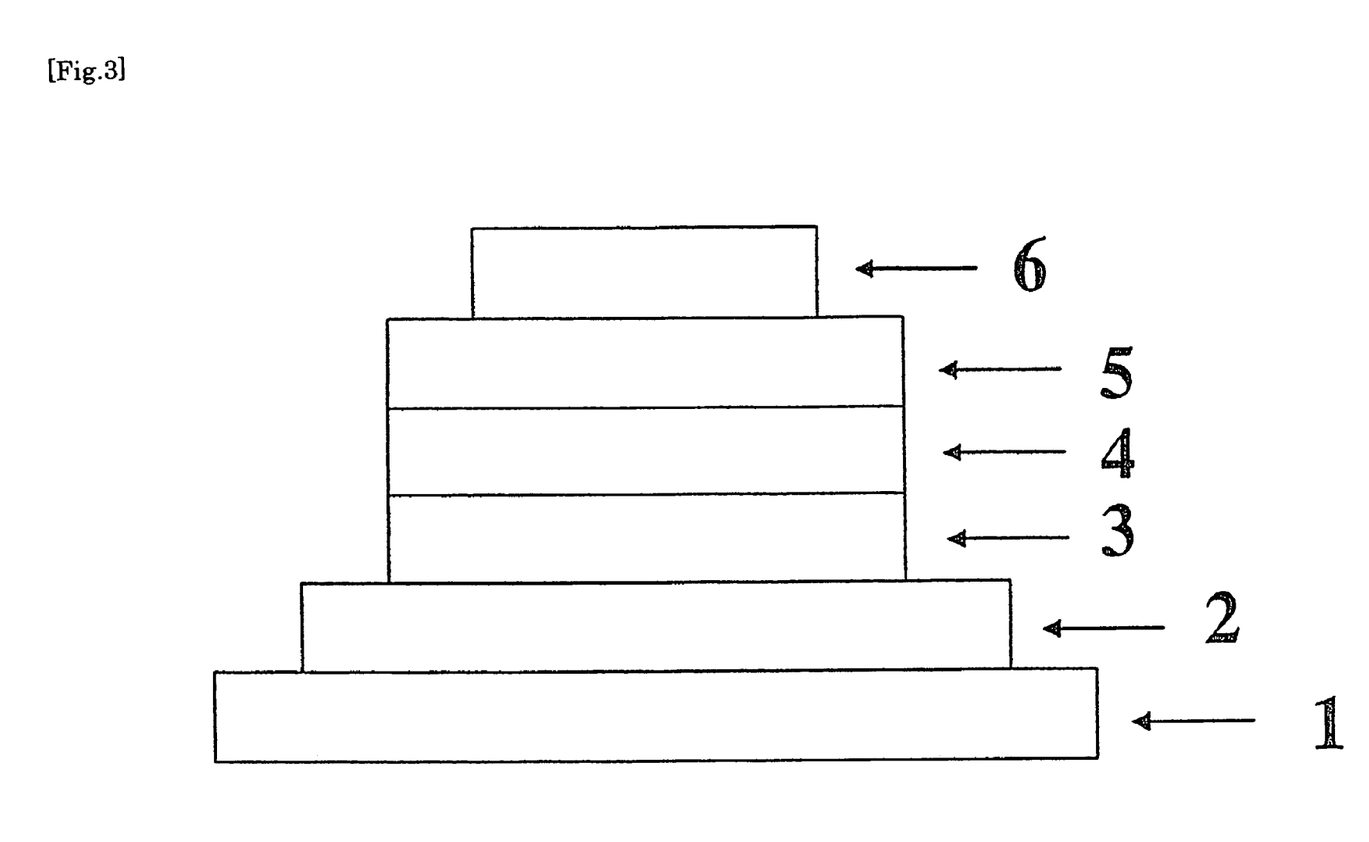
FIG. 3 shows the cross section of an organic EL element prepared according to this invention.

FIG. 3 is a schematic drawing of the cross section of an organic EL element prepared as follows according to this invention.

A cleaned assembly of a glass substrate 1 and an ITO electrode layer 2 with a resistivity of 8-10Ω/□ and an electrode area of 2×2 mm$^2$, available from GEOMATEC Co., Ltd., was placed in a vacuum deposition apparatus of resistance heating type, a 25 nm-thick film of CuPC or a layer 3 was deposited on the ITO layer 2 of the aforementioned electrode-substrate assembly at a degree of vacuum of (7-9)× 10$^{-5}$ Pascal (Pa) while controlling the rate of deposition by a quartz-crystal oscillator type thickness monitor available from ULVAC, and compound No. 2 obtained in Example 1 was deposited in a film thickness of 45 nm on the layer 3 to form a hole-transporting layer 4. In the same vacuum deposition apparatus without breaking the vacuum, Alq3 as a light-emitting material was deposited in a film thickness of 60 nm on the hole-transporting layer 4 to form a light-emitting layer 5. While maintaining the vacuum, a cathode 6 was formed on the light-emitting layer 5 by depositing LiF to a thickness of 6 Å and Al to a thickness of 170 nm.

The electroluminescent elements prepared in this manner were connected to an outside power source and, on application of direct current, confirmed to show luminous properties shown in Table 6. All the elements tested emitted green light. The peak wavelength was 500 nm and this confirmed that only Alq3 emitted light.

Example 4

An electroluminescent element was prepared as in Example 3 with the exception of using compound No. 3 obtained in Example 2 to form the hole-transporting layer. The luminous properties are shown in Table 6.

Comparative Example 1

An electroluminescent element was prepared as in Example 3 with the exception of using NPD to form the hole-transporting layer. The luminous properties are shown in Table 6.

TABLE 6

| | Hole-transporting material | Current density (mA/cm$^2$) @1000 cd/m$^2$ | Voltage (V) @1000 cd/m$^2$ | Luminous efficiency (lm/W) @1000 cd/m$^2$ |
|---|---|---|---|---|
| Comp. Ex. 1 | NPD | 30 | 7.0 | 1.45 |
| Ex. 3 | Compound 2 | 24 | 8.0 | 1.70 |
| Ex. 4 | Compound 3 | 28 | 8.4 | 1.45 |

The durability of these hole-transporting materials was evaluated as follows. Each hole-transporting material alone was deposited on a glass substrate to a film thickness of 1000 Å according to the method shown in Example 3. Thereafter, the film was stored at a temperature of 20° C. and a humidity of 30% and observed visually to determine the number of days for the film to start crystallizing. The results are shown in Table 7.

TABLE 7

| Hole-transporting material | Number of days required for crystallization |
| --- | --- |
| NPD | 25 |
| Compound 2 | 25 |
| Compound 3 | No crystallization even after 100 days |

INDUSTRIAL APPLICABILITY

Organic electroluminescent elements with high glass transition temperature showing high luminous properties and excellent durability can be provided by using specified aminodibenzodioxin derivatives as electroluminescent materials.

What is claimed is:

1. An aminodibenzodioxin compound represented by general formula (1);

(1)

wherein $Ar_1$, $Ar_2$, $Ar_3$, and $Ar_4$ are substituted or unsubstituted aryl groups, and

$Ar_1$, $Ar_2$, and the nitrogen atom bonded thereto, or $Ar_3$, $Ar_4$, and the nitrogen atom bonded thereto, may form a nitrogen-containing heterocyclic ring.

2. The aminodbenzodioxin compound as described in claim 1 wherein $Ar_1$, $Ar_2$, $Ar_3$, and $Ar_4$ are independently any one of phenyl group, naphthyl group, and phenanthryl group, either unsubstituted or substituted with lower alkyl groups, lower alkoxy groups, aryl groups of 4 to 10 carbon atoms, or aryloxy groups of 4 to 10 carbon atoms.

3. An organic electroluminescent element comprising an anode, organic layers, and a cathode piled one upon another on a substrate and comprising the aminodibenzodioxin compound described in claim 1 in at least one of said organic layers.

4. The organic electroluminescent element as described in claim 3 wherein the organic layer comprising the aminodibenzodioxin derivative is selected from the group consisting of a light-emitting layer, hole-transporting layer, and hole-injecting layer.

5. An aminodibenzodioxin compound represented by general formula (1);

(1)

wherein $Ar_1$, $Ar_2$, $Ar_3$, and $Ar_4$ are substituted or unsubstituted aryl groups, and $Ar_1$, $Ar_2$, and the nitrogen atom bonded thereto, or $Ar_3$, $Ar_4$, and the nitrogen atom bonded thereto, forms a nitrogen-containing heterocyclic ring selected from the group consisting of substituted or unsubstituted N-carbazolyl, N-phenoxadinyl, N-phenothiazinyl and N-β-carbolinyl.

6. The aminodibenzodioxin compound as described in claim 5 wherein $Ar_1$, $Ar_2$, $Ar_3$, and $Ar_4$ are independently any one of phenyl group, naphthyl group, and phenanthryl group, either unsubstituted br substituted with lower alkyl groups, lower alkoxy groups, aryl groups of 4 to 10 carbon atoms, or aryloxy groups of 4 to 10 carbon atoms.

7. An organic electroluminescent element comprising an anode, organic layers, and a cathode piled one upon another on a substrate and comprising the aminodibenzodioxin compound described in claim 5 in at least one of said organic layers.

8. The organic electroluminescent element as described in claim 7 wherein the organic layer comprising the aminodibenzodioxin derivative is selected from the group consisting of a light-emitting layer, hole-transporting layer, and hole-injecting layer.

9. The aminodibenzodioxin compound as described in claim 5 wherein $Ar_1$, $Ar_2$, $Ar_3$, and $Ar_4$ are substituted or unsubstituted aryl groups and $Ar_1$, $Ar_2$, and the nitrogen atom bonded thereto or $Ar_3$, $Ar_4$, and the nitrogen atom bonded thereto, may form a N-carbazolyl ring.

* * * * *

UNITED STATES PATENT AND TRADEMARK OFFICE
CERTIFICATE OF CORRECTION

PATENT NO. : 7,605,277 B2  Page 1 of 1
APPLICATION NO. : 10/588373
DATED : October 20, 2009
INVENTOR(S) : Kai et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 432 days.

Signed and Sealed this

Fifth Day of October, 2010

David J. Kappos
*Director of the United States Patent and Trademark Office*

UNITED STATES PATENT AND TRADEMARK OFFICE
CERTIFICATE OF CORRECTION

PATENT NO. : 7,605,277 B2
APPLICATION NO. : 10/588373
DATED : October 20, 2009
INVENTOR(S) : Takahiro Kai et al.

It is certified that error appears in the above-identified patent and that said Letters Patent is hereby corrected as shown below:

On the Title Page, at item (57), Abstract, correct formula (1) to read as follows:

At column 3, line 15, and at column 25, line 20 (claim 1, line 3), correct formula (1) to read as follows:

Signed and Sealed this
Fifth Day of June, 2012

David J. Kappos
*Director of the United States Patent and Trademark Office*